(12) United States Patent
Nollau et al.

(10) Patent No.: US 7,846,746 B2
(45) Date of Patent: Dec. 7, 2010

(54) METHODS OF ANALYSIS AND LABELING OF PROTEIN-PROTEIN INTERACTIONS

(75) Inventors: Peter Nollau, Hamburg (DE); Bruce J. Mayer, Tolland, CT (US)

(73) Assignee: Children's Medical Center Corporation, Boston, MA (US)

( * ) Notice: Subject to any disclaimer, the term of this patent is extended or adjusted under 35 U.S.C. 154(b) by 1118 days.

(21) Appl. No.: 10/474,465

(22) PCT Filed: Apr. 10, 2002

(86) PCT No.: PCT/US02/11272

§ 371 (c)(1),
(2), (4) Date: Mar. 18, 2004

(87) PCT Pub. No.: WO02/083846

PCT Pub. Date: Oct. 24, 2002

(65) Prior Publication Data

US 2004/0157279 A1  Aug. 12, 2004

Related U.S. Application Data

(60) Provisional application No. 60/282,748, filed on Apr. 10, 2001.

(51) Int. Cl.
*G01N 33/543* (2006.01)
(52) U.S. Cl. .......... 436/518; 436/501; 435/7.92; 435/7.93; 435/7.94
(58) Field of Classification Search .......... 435/6, 435/7.1, 7.92–7.94, 333–337, 7.2, 325; 436/501, 436/518, 164, 172
See application file for complete search history.

(56) References Cited

U.S. PATENT DOCUMENTS

| | | | |
|---|---|---|---|
| 4,512,896 A * | 4/1985 | Gershoni ............. | 210/635 |
| 5,352,660 A * | 10/1994 | Pawson ............. | 514/12 |
| 5,665,539 A | 9/1997 | Sano et al. | |
| 5,786,454 A * | 7/1998 | Waksman et al. ......... | 530/402 |
| 5,886,150 A | 3/1999 | Duchesne et al. | |
| 5,985,829 A | 11/1999 | Harris et al. | |
| 5,989,554 A | 11/1999 | Knuth et al. | |
| 6,001,354 A | 12/1999 | Pot et al. | |
| 6,133,428 A | 10/2000 | Wong et al. | |
| 6,197,599 B1 | 3/2001 | Chin et al. | |
| 6,238,869 B1 * | 5/2001 | Kris et al. ............. | 435/6 |
| 6,794,144 B1 * | 9/2004 | Saksela et al. ......... | 435/7.1 |
| 2002/0081570 A1 * | 6/2002 | Lilien et al. ............. | 435/5 |
| 2002/0156236 A1 * | 10/2002 | Kavanaugh et al. ...... | 530/324 |
| 2005/0106631 A1 * | 5/2005 | Roelens et al. ......... | 435/7.1 |

FOREIGN PATENT DOCUMENTS

WO  WO 01/53539 A1  7/2001

OTHER PUBLICATIONS

Pasquali et al., Mapping and identification of protein-protein interactions by two-dimensional far-Western immunoblotting, Electrophoresis 2000, 21, 3357-3368.*
Ingham et al., "The Gab1 Protein Is a Docking Site for Multiple Proteins Involved in Signaling by the B Cell Antigen Receptor," *J. Biol. Chem.* 273(46):30630-30637 (1998).
Jolliffe et al., "Identification of Multiple Proteins Expressed in Murine Embryos as Binding Partners for the WW Domains of the Ubiquitin-Protein Ligase Nedd4," *Biochem. J.* 351:557-565 (2000).
Kaelin Jr., W.G., et al., "Identification of Cellular Proteins That Can Interact Specifically with the T/E1A-Binding Region of the Retinoblastoma Gene Product," *Cell* 64:521-532, Feb. 8, 1991.
Luttrell, D.K. et al., "Involvement of $pp60^{C-SRC}$ with two major signaling pathways in human breast cancer," *Proc. Natl. Acad Sci USA*, 91:83-87, Jan. 1994.
Mayer, B. et al., "The noncatalytic *src* homology region 2 segment of *abl* tyrosine kinase binds to tyrosine-phosphorylated cellular proteins with high affinity," *Proc. Natl. Acad. Sci. USA*, 88:627-631, Jan. 1991.
Ohba, T. et al., "Dot Far-Western Blot Analysis of Relative Binding Affinities of the Src Homology 3 Domains of Efs and Its Related Proteins," *Analytical Biochemistry* 262:185-192, 1998.
Pawson, T. et al., "Protein-protein interactions define specificity in signal transduction," *Genes & Development* 14:1027-1047, 2000.
Ploemen, J.H.T., et al., "Inhibition of Rat and Human Glutathione S-Transferase Isoenzymes by Ethacrynic Acid and Its Glutathione Conjugate," *Biochemical Pharmacology*, 40(7): 1631-1635, 1990.
Rabin, D.U., et al., "An ELISA sandwich capture assay for recombinant fusion proteins containing glutathione-S-transferase," *Journal of Immunological Methods*, 156:101-105, 1992.
Sudol, M., "From Src Homology domains to other signaling modules: proposal of the 'protein recognition code'," *Oncogene* 17:1469-1474, 1998.
Tanaka, S. et al., "C3G, a guanine nucleotide-releasing protein expressed ubiquitously, binds to the Src homology 3 domains of CRK and GRB2/ASH proteins," *Proc. Natl. Acad. Sci.USA*, 91:3443-3447, Apr. 1994.
Walker, J. et al., "Biochemical properties of cloned glutathione S-transferases from *Schistosoma mansoni* and *Schistosoma japonicum*," *Molecular and Biochemical Parasitology*, 61:255-264, 1993.
Wood, E.R., et al., "Quantitative Analysis of SH2 Domain Binding Evidence for Specificity and Competition," *The Journal of Biological Chemistry*, 267(20): 14138-14144, 1992.
Zhao, Z. et al., "Interaction between PAK and Nck: a Template for Nck Targets and Role of PAK Autophosphorylation," *Molecular and Cellular Biology*, 20(11):3906-3917, Jun. 2000.

* cited by examiner

*Primary Examiner*—Melanie Yu
*Assistant Examiner*—Gary W Counts
(74) *Attorney, Agent, or Firm*—Nixon Peabody LLP

(57) ABSTRACT

We have discovered a new method to analyze and characterize complex cell signaling networks. The method is based on specific binding of protein-protein interaction modules to a single type of protein or a mixture of proteins. The method utilizes a number of different protein-protein interaction domains as probes or sensors for the signaling state of the system under investigation.

11 Claims, 16 Drawing Sheets

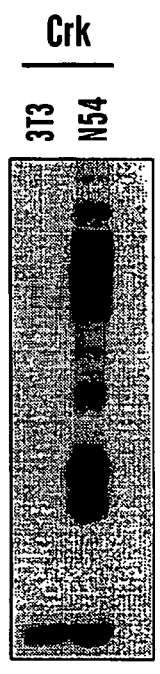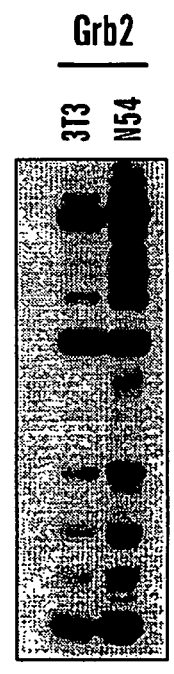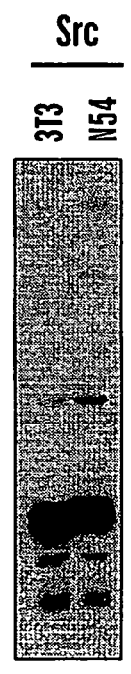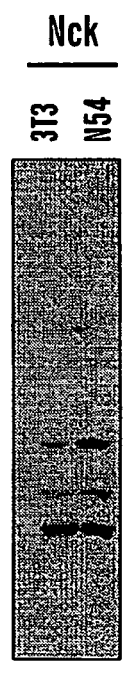
FIG. 4A    FIG. 4B    FIG. 4C

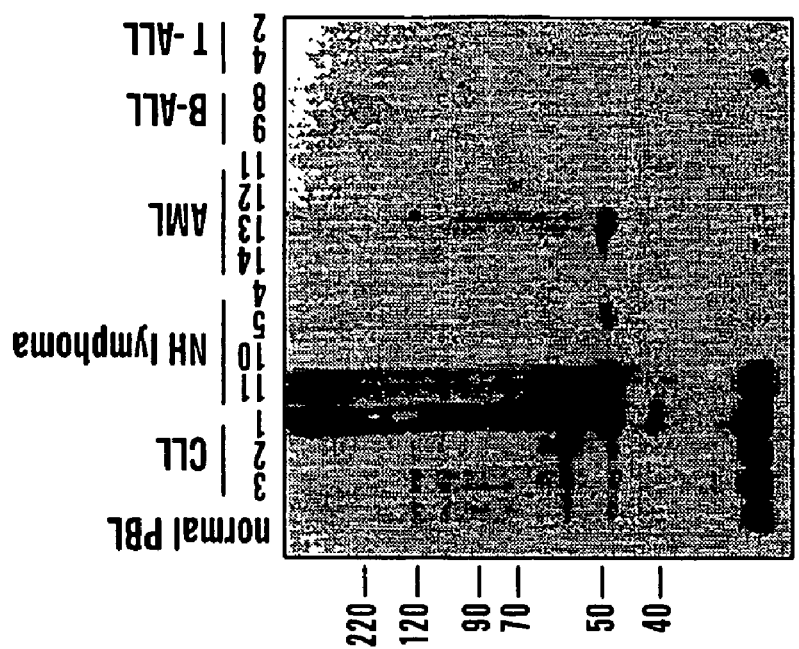
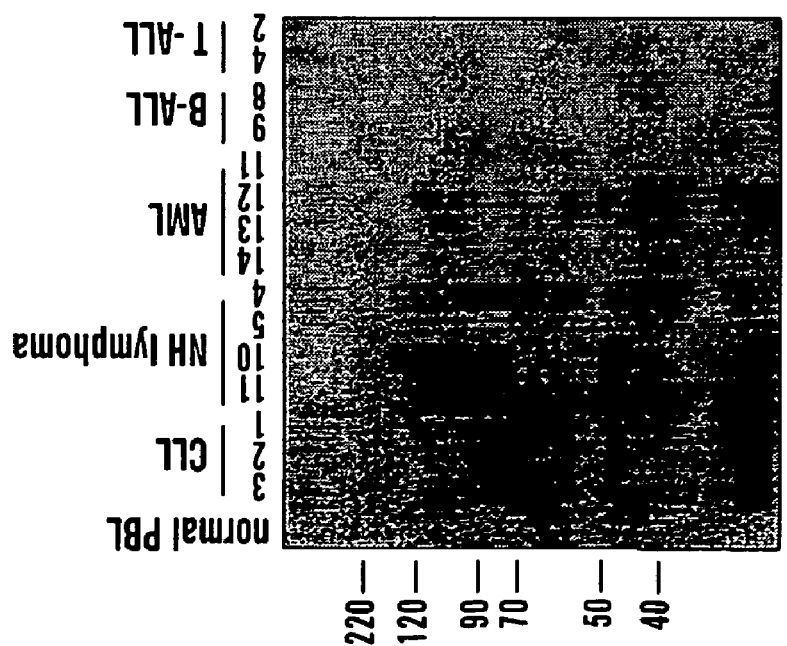
FIG. 5B
FIG. 5A

Glutathione (GSH)

Ethacrynic Acid

Grb2 SH2

GAP SH2s

Fyn SH2 anti-PTyr

METHODS OF ANALYSIS AND LABELING OF PROTEIN-PROTEIN INTERACTIONS

This application is a 371 National Phase Entry Application of co-pending International Application PCT/US02/11272 filed on 10 Apr. 2002 which designated the U.S and which claims the benefit of U.S. Provisional Application 60/282,748 filed 10 Apr. 2001.

GOVERNMENT FUNDING

This invention was made with government support under 1 R01 CA82258-01 awarded by the National Institutes of Health. The government has certain rights in the invention.

FIELD OF THE INVENTION

The present invention relates generally to cell signaling, and particularly to methods for analyzing and labeling protein-protein interactions.

BACKGROUND

Important cellular functions like proliferation, differentiation, gene expression, cytoskeletal organization or cell survival depend on extracellular signals which lead to the activation of intracellular signaling pathways followed by a specific response appropriate for the biological needs of the cellular system. Signaling involves a large number of different proteins, and specific protein-protein interactions are a key event in the transduction of extracellular signals to the inside of the cell. Many signaling molecules contain domains also called protein-protein interaction modules (e.g. SH2-, SH3-, PTB-, PDZ- or WW-domains) composed of approximately 40 to 160 amino acids which can be separated from the original protein without loss of binding function. These domains contain ligand-binding surfaces that specifically interact with short linear sequence motifs (3 to 10 amino acids) in the complementary binding partners by which downstream signaling is mediated. Tyrosine-phosphorylated proteins involved in signaling are, for example, recognized by SH2- or PTB-domains and the specificity of the interaction is determined by the amino acid composition of the core binding site in the binding partner (pYxx$\Psi$ for SH2- or NPxpY for PTB-domains where pY=phosphotyrosine, N=asparagine, P=proline, $\Psi$=hydrophobic amino acids and x stands for any or selected amino acids which are important for the interaction). In contrast, SH3- or WW-domains bind to proline-rich sequences with the general consensus sequence $\Psi$px$\Psi$P for SH3-domains and the specificity of the interaction is additionally dictated by N-terminal or C-terminal localized amino acids flanking the core sequence. Binding affinities of these protein-protein interactions are in the range of $10^{-8}$ to $10^{-5}$ M (1, 2).

Existing Labeling and Detection Techniques

Today, a major problem in the detection of protein-protein interactions is the specific and efficient labeling of the protein-protein interaction domains. Different experimental approaches can be used for the labeling of protein-protein interaction domains. Labeling or tagging can either be performed before or after the purification of the recombinant expressed protein. Labeling of protein-protein interaction domains by biotin or $^{125}$I after the step of protein purification has been described previously (3, 4). A major disadvantage of covalent coupling methods is the control and unpredictable outcome of the labeling reaction. Inappropriate or overextensive labeling results in the loss of function of the binding protein and increased background, while low levels of labeling result in weak signals.

Moreover, labeling efficiency will vary between protein-protein interaction domains as the number of reactive groups for coupling differ from domain to domain making the standardization of labeling and the subsequent quantification of binding interactions problematic. As the labeling conditions have to be determined experimentally for each domain, covalent labeling of recombinant proteins is not appropriate for the analysis of signaling networks, especially when a large number of differently labeled protein-protein interaction domains is needed.

Protein-protein interactions can also be detected without previous labeling e.g. by antibodies directed against the protein-protein interaction domain. Luttrell et al. used anti-src antibodies for the detection of the interaction of the src-SH2 domain with cellular proteins in a Far-Western blot (5). For the present invention, this approach is not appropriate, as a large number of non-crossreacting highly specific antibodies are needed which are not necessarily available. In addition, quantification of the protein-protein interactions is difficult, as the different antibodies will vary in their binding affinities resulting in variable signal intensities.

Alternatively, protein-protein interaction can be detected by tags that are expressed as parts of the fusion protein and are used for purification or are inserted in the fusion protein in addition to the purification tag. Kaelin et al. inserted the phosphorylation site of protein kinase A allowing the subsequent $^{32}$P-labeling of fusion proteins (6). Recently, Zhao et al. presented a vector system in which ras is inserted between the N-terminal localized GST-purification tag and C-terminal SH3-domains (7). Incubation of [$\gamma$-$^{32}$P]GTP with the fusion protein results in the labeling of ras by which protein-protein interactions are detected. These approaches allow the uniform labeling of protein-protein interaction domains by radioactivity with the major disadvantage that only one label is available, so differential labeling of different domains cannot be achieved. Moreover, in the method described by Zhao et al. dissociation of the label will occur as the binding of GTP is not covalent. This results in the labeling of other protein-protein interaction domains that are supposed to behave as unlabeled competitors when this labeling method is applied to the competitive assay outlined in the invented approach.

Application of GST-Antibodies for the Detection of GST-Fusion Proteins

Additionally to the labeling and detection methods described above, protein-protein interactions can be directly detected by the purification tag, by using antibodies directed against the purification tag. This method has been used by Tanaka et al. for the detection of protein interactions applying GST-fusion proteins (8). We tested this approach for the detection of single SH2-domain interactions with cellular proteins in a Far-Western blot (FIG. 2). Protein lysates of 3T3 fibroblasts and v-abl transformed 3T3 fibroblasts were used as a model system and investigated in parallel. Due to the uncontrolled kinase activity of v-abl, strong tyrosine phosphorylation occurred in the v-abl transformed 3T3 fibroblasts in contrast to the untransformed cells. The difference in the extent of tyrosine phosphorylation between the two cell lysates can be demonstrated with the commonly applied antibody 4G10 which recognizes a broad spectrum of tyrosine phosphorylated proteins (FIG. 2A). For the Far-Western blot analysis, whole cellular lysates were prepared from both cell lines, applied in equivalent amounts to SDS-PAGE and proteins were transferred to PVDF-membranes. Incubation of the membrane was performed with a recombinant expressed GST-abl-SH2 domain or GST alone as a control. GST fusion is widely used for the expression and purification of recombinant proteins and GST-fusion proteins have already been successfully applied for the study of protein-protein interactions. After binding and washing, protein-protein interactions were detected by chemiluminescense (ECL) with an anti-GST mouse antibody directed against the non-denatured form of GST followed by incubation with a horseradish-peroxidase (HRP) labeled goat anti-mouse antibody. As demonstrated in FIG. 2B, differences in the tyrosine phoshorylation pattern of 3T3 and v-abl transformed 3T3 cells are detectable, similar to the pattern obtained with the 4G10 phosphotyrosine-specific antibody. However, the high background that was observed in the GST control made this approach very problematic for the quantification and precise identification of differences in signal transduction patterns. Comparable results with high levels of background were also observed when the biotinylated GST-abl-SH2-domain was used as a probe and detection was performed with streptavidin-HRP (FIG. 2C). Additionally, the usefulness of the currently-available labeling systems (e.g. anti-GST antibody) for molecular diagnostics is severely limited because the low signal-to-noise results produced by these systems make it impossible to detect specific signals in cells, with few exceptions (such as the N54 cells which contain very high levels of tyrosine phosphorylation).

The qualitative and quantitative characterization of complex signaling networks and the identification of major cell type specific signaling proteins is very important because it would enable understanding of physiological processes of signal transduction and alterations of signaling in a multitude of human diseases such as cancer, autoimmunological diseases and other disorders. Detailed insights in signaling networks and the identification of disease-associated differences in signaling may lead to new ways for the rational design and development of specific drugs. The pattern of binding interactions in a cell or tissue may also be used as a tool for molecular diagnostics, for example in classifying tumors.

In general, signal transduction pathways and specific protein interactions are investigated by classical methods like Western blot analysis, Far-Western blot or co-immunoprecipitation studies as well as application of protein expression libraries or the two-hybrid assay system. In most of these applications single protein-protein interactions are studied. Techniques allowing the analysis of signaling networks do not currently exist. New methods for the analysis and characterization of complex cellular signaling networks are needed.

SUMMARY OF THE INVENTION

We have discovered a new method to analyze and characterize complex cell signaling networks. The method is based on specific binding of protein-protein interaction modules to a single type of protein or a mixture of proteins. The method utilizes a number of different protein-protein interaction domains as probes or sensors for the signaling state of the system under investigation.

In one embodiment there is provided a method for determining binding of a selected protein-protein interaction domain to a protein obtained from a biological specimen. The method includes (a) obtaining a protein mixture from the biological specimen; (b) immobilizing the protein mixture to a solid support; (c) contacting the immobilized protein mixture with a plurality of unlabeled protein-protein interaction domains under appropriate binding conditions; (d) simultaneously with or subsequent to step (c) contacting the immobilized protein mixture with at least one labeled selected protein-protein interaction domain, the labeled protein-protein interaction domain being different from the unlabeled protein-protein interaction domains; and (e) measuring the binding of the labeled protein-protein interaction domain.

Preferably, the solid support contemplated in the method includes a membrane, a plastic, or a bead. Preferably, the proteins in the protein mixture of the method are denatured or non-denatured. Preferably, the protein-protein interaction domains are selected from the group consisting of zinc finger, RING finger, WD40 repeat, armadillo repeat, ankyrin repeat, SH2-, SH3-, PTB-, PDZ-, WW-, EH-, LIM-, TPR-, SAM-, EVH1- or other modular domains. More preferably, the protein-protein interaction domains are SH2- or SH3-domains. The protein-protein interaction domains can also be fusion proteins. A concentration of the labeled and unlabeled protein-protein interaction domains is preferably greater than that of the protein mixture. Preferably, a single protein-protein interaction domain selected for binding is labeled. More preferably, a plurality of protein-protein-interaction domains selected for binding are differentially labeled. The label contemplated in the method includes a biotinylation sequence, an antibody recognition sequence, and a fluorophore. Preferably, the label is glutathione-S-transferase (GST).

In a second embodiment of the invention, there is provided a method for determining binding of protein-protein interaction domains to a protein obtained from a biological specimen. The method comprises (a) obtaining a protein mixture from the biological specimen; (b) immobilizing the protein mixture to a solid support; (c) contacting the immobilized protein mixture with a plurality of labeled protein-protein interaction domains under appropriate binding conditions; and (d) measuring the binding of the labeled protein-protein interaction domains. Preferably, the protein-protein interaction domains are labeled with oligonucleotides. Preferably, the oligonucleotides comprise nucleic acid analogs. The oligonucleotides that can be used in the method of the invention include DNA-oligonucleotides, protein nucleic acids, RNA oligonucleotides, and thioester derivatives.

In a third embodiment of the invention, there is provided a construct comprising a protein and an oligonucleotide, wherein the oligonucleotide further comprises two flanking sequences that can be used as primer binding sites for PCR-amplification, and an internal sequence interposed between the two flanking sequences. The internal sequence is preferably different for a selected protein. The oligonucleotide that can be used in the construct includes a DNA-oligonucleotide, a protein nucleic acid, an RNA oligonucleotide, a nucleic analog, or a thioester derivative. Preferably, the protein to be used in the construct is a protein-protein interaction domain.

In a fourth embodiment of the present invention, there is provided a method for detection of GST-fusion proteins. The method includes labeling a single glutathione-S-transferase (GST) fusion protein with a glutathione (GSH) conjugate wherein the GSH conjugate is non-covalently coupled to the GST fusion protein. Preferably, the GSH conjugate comprises a horseradish peroxidase (HRP).

In a fifth embodiment there is provided a method of producing inert protein-protein interaction domains. The method comprises the steps of (a) incubating the protein-protein interaction domains in a reaction mixture with GSH and ethacrynic acid; (b) subsequently to incubating, removing unbound molecules of low molecular weight; and (c) separating unconjugated protein-protein interaction domains from the reaction mixture by binding the unconjugated protein-protein interaction domains to a substrate. Preferably, the protein-protein interaction domains are GST-fusion proteins. Preferably, the substrate is a GSH-sepharose bead.

Finally, there is provided a method of carrying out a multiplex binding assay for the analysis of a biological specimen. The method comprises (a) incubating inert protein-protein interaction domains produced by the method of the invention as described in the fifth embodiment with a plurality of labeled molecules; and (b) measuring the binding of the labeled molecules. Preferably, the molecules are protein-protein interaction domains, proteins, or antibodies. Preferably, the label is an oligonucleotide or a fluor.

BRIEF DESCRIPTION OF THE DRAWINGS

FIGS. 4A-4C are Far-Western blot analyses with different protein-protein interaction domains labeled with the GSH-HRP conjugate. Binding of the SH2-domains of Crk or Nck, the SH3-domains of Abl, Src or Nck and a GST-fusion protein composed of the SH2- and SH3 domain of Grb2 was analyzed on different membranes with lysates of 3T3- and v-abl transformed 3T3-cells (NS4).

FIGS. 5A-B are a Far-Western blot analysis of whole cellular lysates of different human leukemia with the GSH-HRP labeled SH2-domains of Abl (FIG. 5A) and Crk (FIG. 5B), respectively.

DETAILED DESCRIPTION

Figure 1:
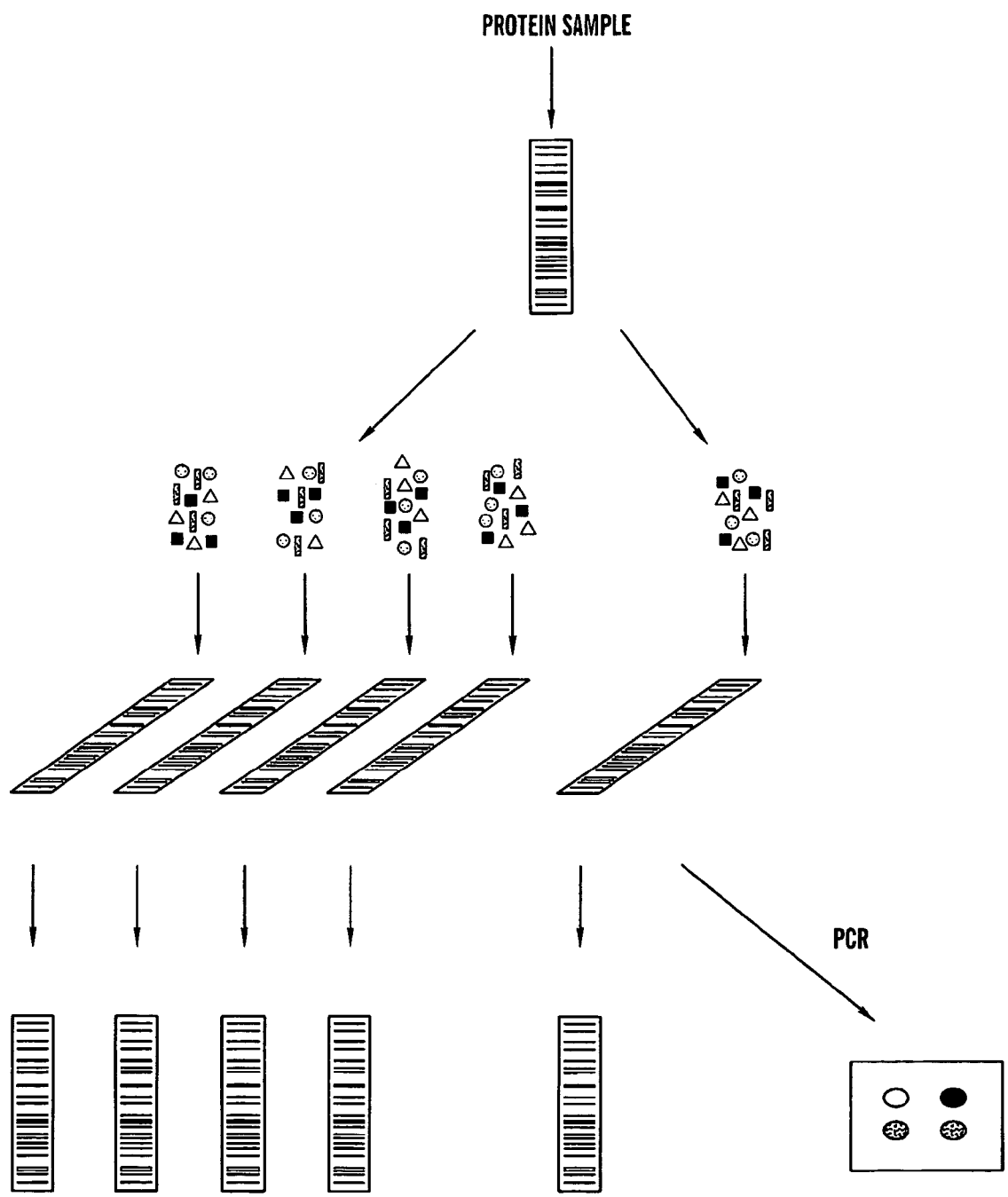
FIG. 1 depicts a general principle of the competitive binding assay of the present invention with different labeling and detection strategies.

One embodiment of the present invention is summarized in FIG. 1 and the different components of the assay system are described in detail below:

Protein Sample

The assay of the present invention can be applied to any kind of protein sample. Proteins can be derived from any biological specimen including, but not limited to, tissues, body fluids, cell cultures or generated by recombinant expression methods. In one embodiment, preparation of whole cellular proteins from tissues, body fluids or cell cultures is performed by standard methods used in the art. In another embodiment, proteins are produced, for example, by in vitro transcription-translation systems, by recombinant expression systems or are already expressed on the surface of microorganism or cells (e.g. expression libraries). Depending on the experimental objective and the type of protein-protein interaction under investigation, proteins can be analyzed either in their denatured or non-denatured from.

Solid Surface for Immobilization

The proteins in which signaling networks are analyzed are immobilized on solid support surfaces, including, but not limited to, membranes (e.g. PVDF or nitrocellulose), plastic surfaces (e.g. polystyrene) or can be covalently coupled to appropriate beads (e.g. Epoxy-activated beads). The binding or coupling of proteins to solid surfaces is performed by standard methods ("Antibodies, a Laboratory Manual." Harlow, E., and Lane, D., eds. Cold Spring Harbor Press, Cold Spring Harbor N.Y., 1988). For example, protein samples can be directly spotted on a membrane (dot/slot blot) or separated by conventional SDS-PAGE prior to the transfer on a membrane. Separation of proteins prior to analysis will provide qualitative in addition to quantitative information that will be helpful for the characterization of protein-protein interaction profiles and identification of specific binding partners especially when complex protein mixtures like clinical samples are investigated.

Protein-Protein Interaction Domains

Any protein-protein interaction module can be utilized in the method of the present invention. Domains are preferably generated by recombinant expression technologies and are preferably fusion proteins (e.g., GST-fusion proteins) allowing their purification from bacterial or other contaminating proteins depending on the expression system. For the competitive binding reaction, the different protein-protein interaction domains are applied, preferably, in equimolar concentrations, or otherwise as appropriate to the biological objective. The concentration of the binding domains is, preferably, in large excess (e.g., from 1 nanomolar to 10 micromolar) over the corresponding immobilized binding partners, as interacting molecules, for example, isolated from cells are generally present in low concentrations in comparison to the whole amount of cellular proteins.

Binding is preferably performed in known buffer systems, most preferably in buffer systems that have already been used for studies of protein-protein interactions (e.g. TBST-buffer). Depending on the affinity and the type of the domain the reaction is preferably carried out at room temperature or 4C. Reproducible signals are generally obtained quickly, e.g., in approximately one hour, including the steps of binding, washing and detection.

At present, approximately 145 different human SH2-domains and 276 different human SH3-domains have been described and can be applied to the assay. With the completion of the human genome project the entire collection of the large number of protein-protein interaction modules will be available in the near future (2). The method of the present invention is not limited to modules of human origin and depending on the biological objective signaling modules of any species can be applied.

Labeling of Protein-Protein Interaction Modules

For the detection and characterization of specific protein-protein interactions, each protein-protein interaction domain applied in the method of the present invention is preferably labeled. Depending on the labeling strategy, the competitive binding assay can be performed in two different ways. In one embodiment of the invention, only one domain is labeled while all other domains in the reaction mixture remain unlabeled. Under these conditions, several independent binding reactions must be performed with the same immobilized protein to compare the patterns with different binding domains. The number of separate binding experiments depends on the number of the protein-protein interaction domains that are applied for the assay. The different binding reactions can be performed either in parallel (for example, with multiple filters on which the same type and amount of protein is immobilized) or by repeated cycles of binding (for example, with, the same filter after the removal of the labeled domain which was applied in the previous binding reaction).

Labeling of single domains and their detection can be achieved in several ways. Simply, the domain or tag that is fused to the protein-protein interaction domain and is used for purification can be used for detection (e.g. glutathione-S-transferase (GST) tag) or additional tags like biotinylation or antibody recognition sequences can be added to the fusion gene by recombinant DNA-technologies. Alternatively, protein-protein interaction domains can be labeled after purification e.g. by biotinylation or by the covalent attachment of fluorophores. The advantages and disadvantages of the different labeling strategies will be discussed in more detail above.

In another embodiment of the present invention, all protein-protein interaction domains participating in the binding reaction are labeled with different tags. This approach has the advantage of having all relevant protein-protein interactions quantitatively determined in a single binding experiment. However, this approach is limited by the number of different tags or labels which are available or can be specifically detected, especially when a large number of protein-protein interaction domains are applied for the competitive binding assay. To overcome this problem, in another embodiment of the present invention, protein-protein interaction domains are tagged with different oligonucleotides such as DNA-oligonucleotides and nucleic acid analogs, e.g., protein nucleic acids, RNA oligonucleotides, thioester derivatives. Each oligonucleotide is composed of two flanking sequences that are identical for each protein-protein interaction domain and are used as primer binding sites for subsequent PCR-amplification. Preferably, an internal sequence is interspersed between the two flanking sequences, which is different for each protein-protein interaction domain thereby defining the domain. Methods for the attachment of individual oligonucleotides to their corresponding protein-protein interaction domains are described below.

After the binding reaction, bound protein-protein interaction domains are eluted from the solid surface and amplified by PCR with the primers corresponding to the flanking sequences. Preferably, one primer is labeled e.g. by biotin or fluorescein resulting in the labeling of the PCR products. After amplification, relevant protein-protein interactions are quantitatively determined by applying the labeled and denatured PCR products to, for example, a reverse dot blot or DNA-chip on which the complementary oligonucleotides corresponding to the internal sequences are immobilized. The different protein-protein interaction domains are identified and quantitated by their unique internal sequence and the position on the reverse dot blot or DNA-chip to which the PCR-product is binding.

Comparison of the Methods of the Present Invention to Existing Methods

The method of the present invention is a further novel improvement of already established techniques like the Far Western blot or other filter binding assays. In these prior methods, immobilized proteins are incubated with labeled protein-protein interaction domains allowing the qualitative and/or quantitative determination of binding interactions. One major difference between the present invention and already existing methods is the application of a large number of different domains reacting in a competitive fashion in the same binding reaction and the development of appropriate labeling techniques for this purpose. In contrast to previously published methods in which only single domains were applied for the binding reaction, the method of the present invention has the potential of preferentially detecting specific, high affinity interacting proteins as a large number of protein-protein interaction domains compete for their corresponding binding partners in the same reaction. This is very important for protein-interaction modules (for example, SH2) as different specific domains have overlapping binding specificity, so when binding assays are performed in the absence of a competitor, one is likely to detect interactions that do not occur in vivo where many binding domains compete for binding to targets.

Novel Method for the Detection of GST-Fusion Proteins

Figure 3:
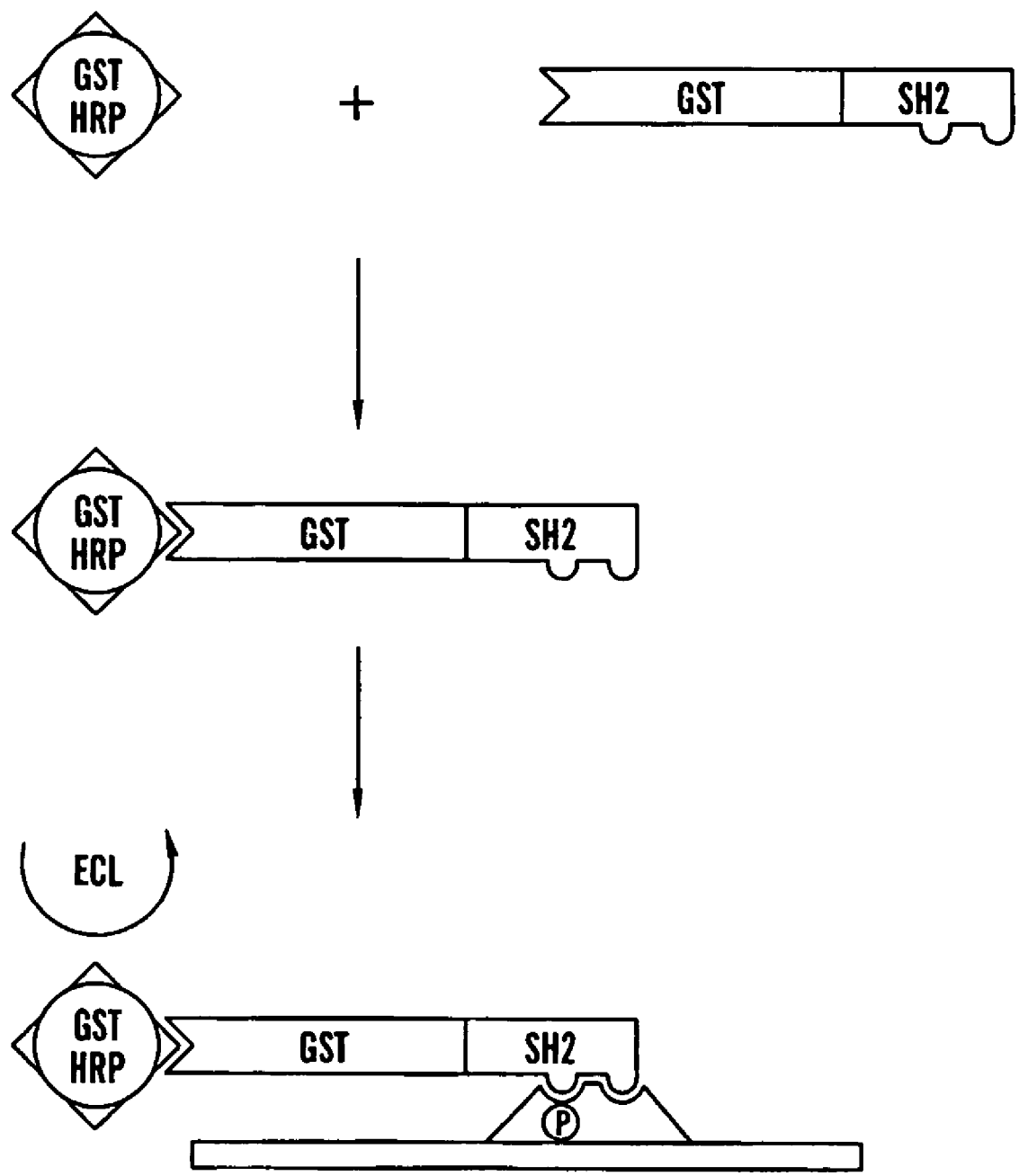
FIG. 3 shows labeling of GST-fusion proteins with the glutathione horseradish peroxidase conjugate (GSH-HRP). After binding of the labeled SH2-domain to tyrosine-phosphorylated proteins (P) immobilized on a solid surface signals are detected by chemiluminescence (ECL).

To overcome the technical problems of labeling and detection of the prior art, we invented a new method for the detection of GST fusion proteins. The method is based on the specific binding of glutathione (GSH) to GST, allowing the labeling of GST fusion proteins with a glutathione horseradish peroxidase conjugate (GSH-HRP). The labeling method and its application are illustrated in FIG. 3. However, GSH can be conjugated with any other substance that can chemically cross-link to GSH and therefore be used for labeling. GSH-HRP is commercially available (e.g. Sigma), relatively stable and inexpensive, and has previously been used for the detection of GST fusion proteins in enzyme linked assays or dot blots (9).

Figure 2A:
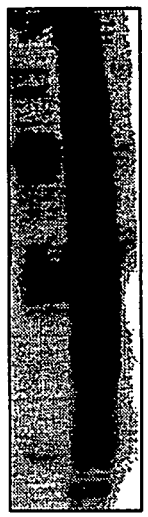
FIGS. 2A-2D show detection of tyrosine-phosphorylation pattern in 3T3- and v-abl transformed 3T3-fibroblasts (N54) by Far-Western blot analysis using the phosphotyrosine-specific monoclonal antibody 4G10 (FIG. 2A), an antibody specific for GST (FIG. 2B), a biotin labeling (FIG. 2C), and by the invented labeling method applying the glutathione horseradish peroxidase (GSH-HRP) conjugate (FIG. 2D). For FIGS. 2B and 2D, membranes were incubated with the Abl-GST fusion protein or GST alone as control and protein interactions were subsequently detected by the anti-GST antibody or with GSH-HRP labeled Abl.
Figure 2B:
Figure 2B:
Figure 2C:
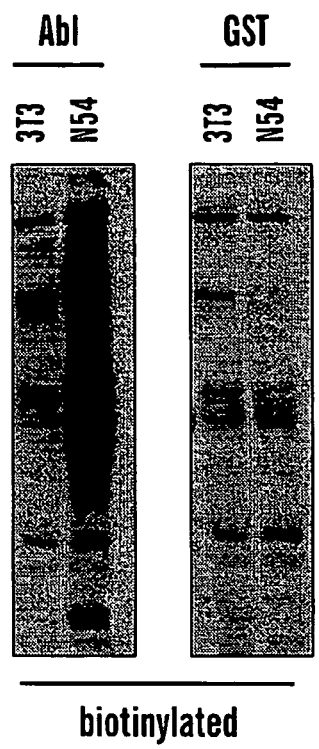
Figure 2D:
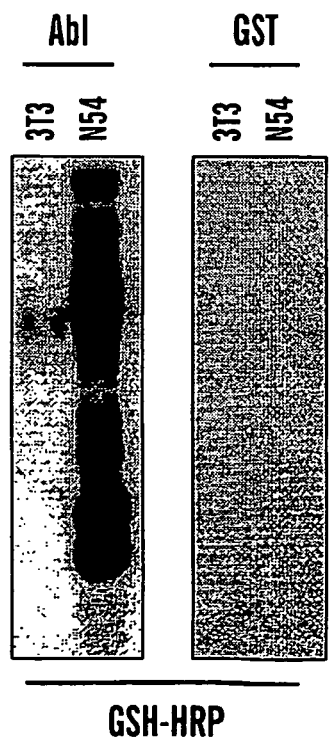

To apply this labeling technique for the detection of protein-protein interactions, the GSH-HRP conjugate was pre-incubated for a short time period with single protein interaction domains fused to GST. The reaction mixture was then directly applied without further purification to membranes on which lysates of 3T3 and v-abl transformed 3T3 cells were transferred as described before. After incubation and washing which can be performed in less than one hour, signals are directly detected by chemiluminescence. As illustrated for the Far Western blots in FIG. 2D and FIG. 4, strong and specific signals are obtained with different SH2 or SH3 domains and virtually no background is detectable when the assay is performed with GST alone (FIG. 2D).

The same assay was applied in pilot experiments to whole cellular protein lysates derived from various types of human leukemia (FIGS. 5A and B). Different patterns of tyrosine phosphorylated binding sites were detectable in different types of leukemia when abl-SH2 or crk-SH2 were used as probes for the detection of protein-protein interactions. Signals were at best barely detectable when the phospho-tyrosine specific antibody 4G10 was applied to the same filters (data not shown), indicating that patterns of tyrosine phosphorylation can be detected with very high sensitivity and specificity when labeling of GST-fusion proteins was performed with the GSH-HRP conjugate.

The detection method of the present invention can be applied easily, rapidly and efficiently to detect any protein-protein interaction in which GST-fusion proteins are used. While not wishing to be bound by theory, the low background level achieved by this method is most likely due to the labeling of only that fraction of fusion proteins in the preparation which are correctly folded and, therefore, functionally intact and capable of binding the GSH-HRP conjugate. In many other labeling and/or detection techniques all fusion proteins are detected regardless of their functional state which indicates that the higher background levels achieved by these methods are due to the denatured and/or aggregated probe.

The non-covalent attachment of the GSH-HRP conjugate to GST-fusion proteins can be problematic when the binding reaction is performed with many different protein-protein interaction domains, for example, a competitive assay of the present invention. In this situation, the GSH conjugate can dissociate from the labeled domain and bind to other competing GST fusion proteins in the reaction mixture, making the precise determination and quantification of interactions mediated by a single domain impossible. To solve this problem, we have invented an additional method of blocking GSH binding sites in competitors via a covalent attachment of GSH to GST fusion proteins.

Novel Method for Blocking and Covalent Coupling of GSH to GST

Figure 6:
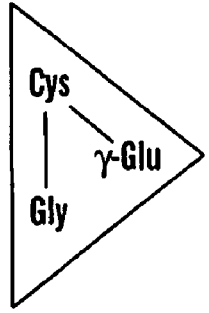
FIG. 6 is a model for the covalent coupling of GSH via the sulfhydryl group to GST-fusion proteins by ethacrynic acid (EA). The unsaturated ketone moiety of EA covalently reacts with different amino acids in the substrate binding pocket of GST.
Figure 6:
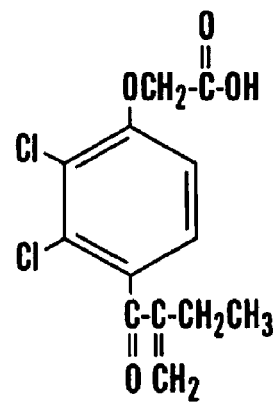
Figure 6:
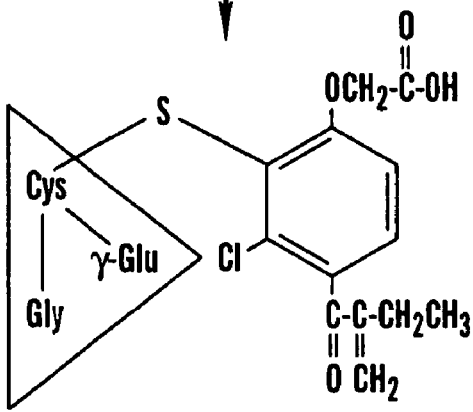
Figure 6:
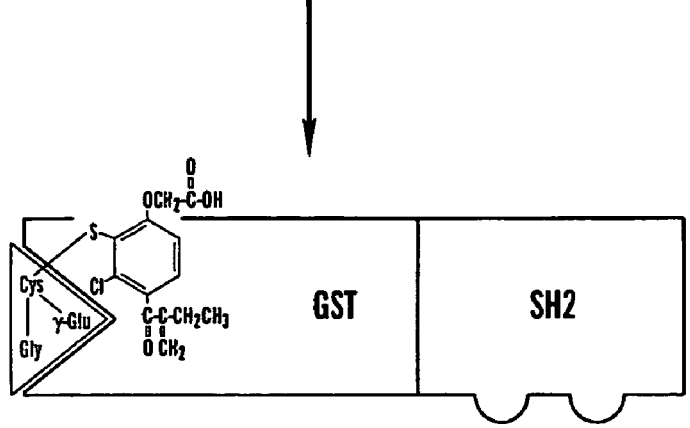
Figure 7:
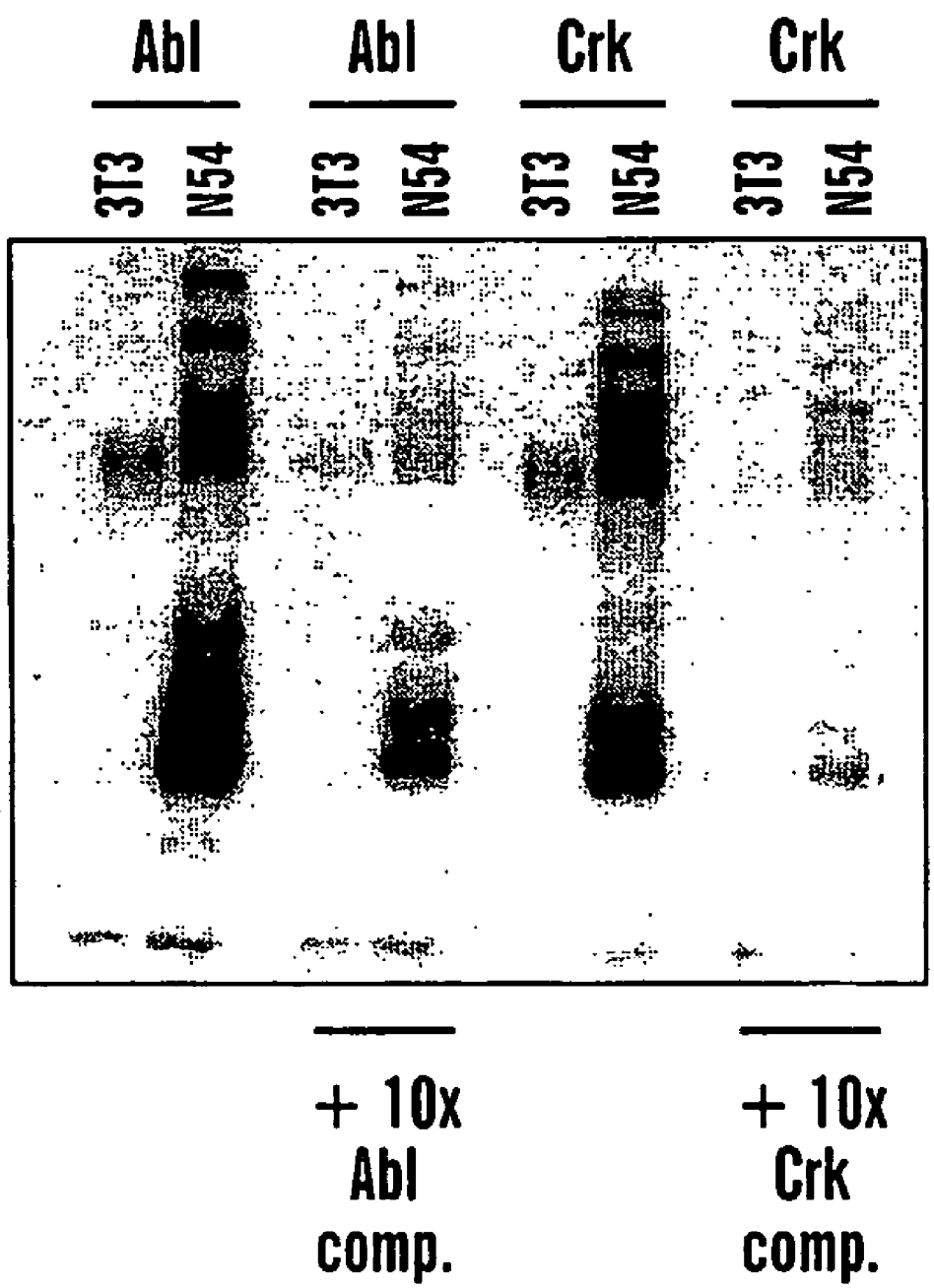
FIG. 7 depicts competition of the binding of the GSH-HRP labeled SH2-domains of Abl or Crk by their corresponding domains blocked for the binding of GSH-HRP after conjugation with glutathione and ethacrynic acid. The competitors (comp.) were applied in 10-fold excess over the concentration of the labeled SH2-domain. Far-Western blots were performed with lysates isolated from 3T3- and v-abl transformed 3T3-cells (N54).

Glutathione-S-transferases make up a large group of isoenzymes that play an important role in the detoxification by catalyzing the conjugation of GSH to a large number of toxic compounds (9). Ethacrynic acid is known as a potent inhibitor of GST and is assumed to block the enzymatic activity of GST by covalent binding as a glutathione-ethacrynic acid conjugate to the catalytic domain of GST (10). We used the properties of ethacrynic acid for the covalent attachment of GSH to GST-fusion proteins thereby blocking the ability of the competitors to bind to the GSH-HRP conjugate in the subsequent binding reaction (FIG. 6). For this purpose, the protein-protein interaction domain (GST-fusion protein) is incubated with GSH and ethacrynic acid, respectively. After the reaction, unbound molecules of low molecular weight (GSH and ethacrynic acid) are removed, for example, by gel filtration and unconjugated GST-fusion proteins are separated from the reaction mixture by binding to, for example, GSH-Sepharose beads. Applying this method, we obtained GSH-ethacrynic acid conjugated GST-fusion proteins that were stable for several days at 4° C. or after repeated cycles of freezing and thawing with respect to the conjugation (data not shown). To test the ability of the conjugates to compete with labeled protein-protein interaction domains, we co-incubated SH2-domains labeled with GSH-HRP with SH2-domains in which the binding for GSH-HRP was blocked by GSH-ethacrynic acid conjugation. Binding of the labeled abl or crk SH2 domain was greatly reduced in the Far-Western blots when the corresponding GSH-ethacrynic acid conjugated domains were applied in a tenfold excess over the labeled domain (FIG. 7). These results demonstrate that the unwanted binding of GSH-HRP to competing domains can be simply and efficiently blocked by the preincubation of the competitors with GSH and ethacrynic acid.

Figure 8A:
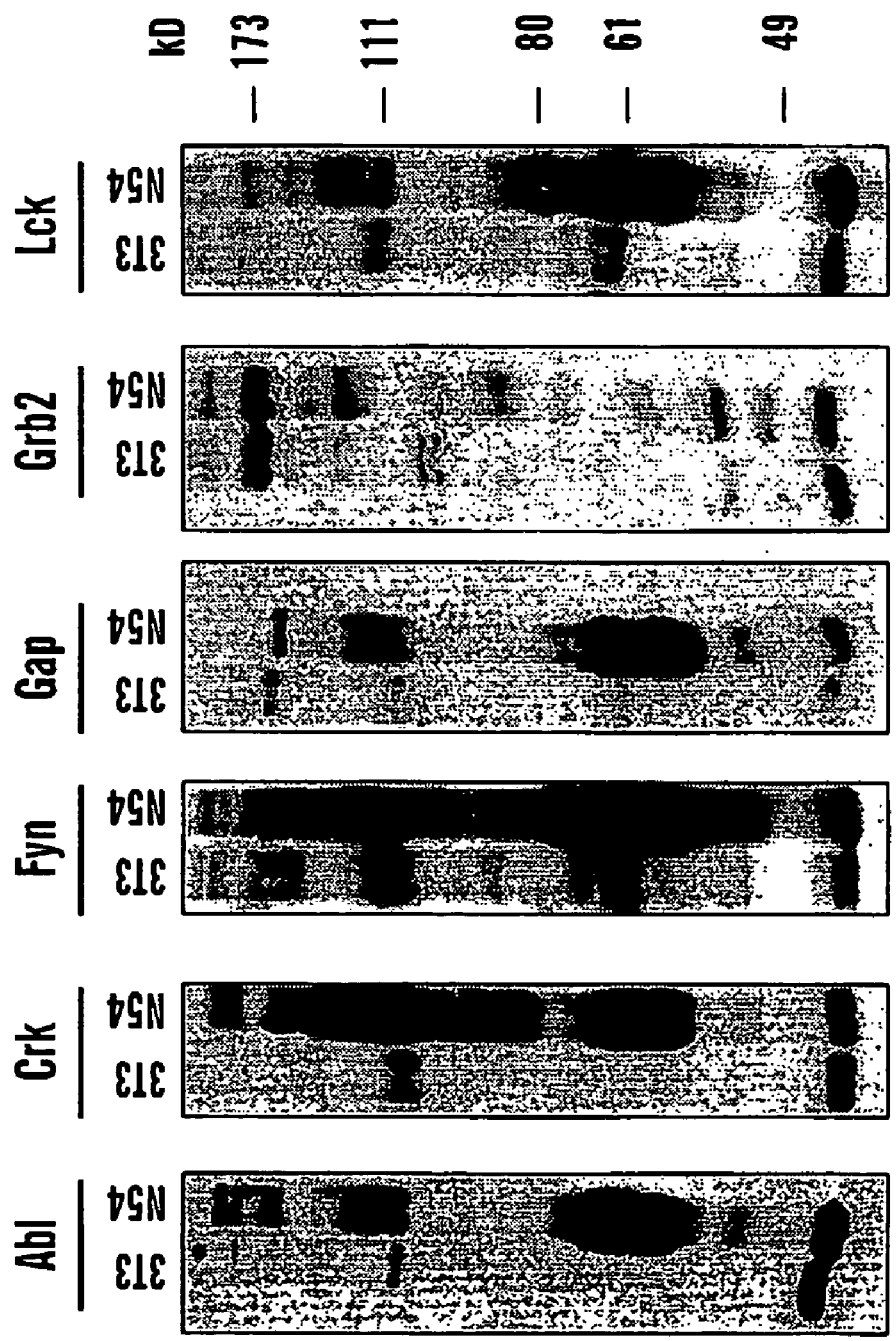
FIGS. 8A-B are a Far-Western blot analysis with 12 different SH2 domain probes under competitive and non-competitive binding conditions. Protein extracts (80 mg/lane) of 3T3 fibroblasts and v-abl transformed 3T3-cells (N54) were separated by SDS-PAGE and transferred to PVDF membranes. After blocking the membrane was cut in strips and individual filter strips were probed for 15 min at room temperature with the GSH-HRP-labeled SH2 domains at a concentration of 1 mg/ml. For the competitive analysis, binding reactions were performed with one labeled domain in the presence of equimolar amounts of all other 11 domains previously blocked by GSH-ethacrynic acid treatment. After washing, signals were detected by ECL (exposure 1 min).
Figure 8B:
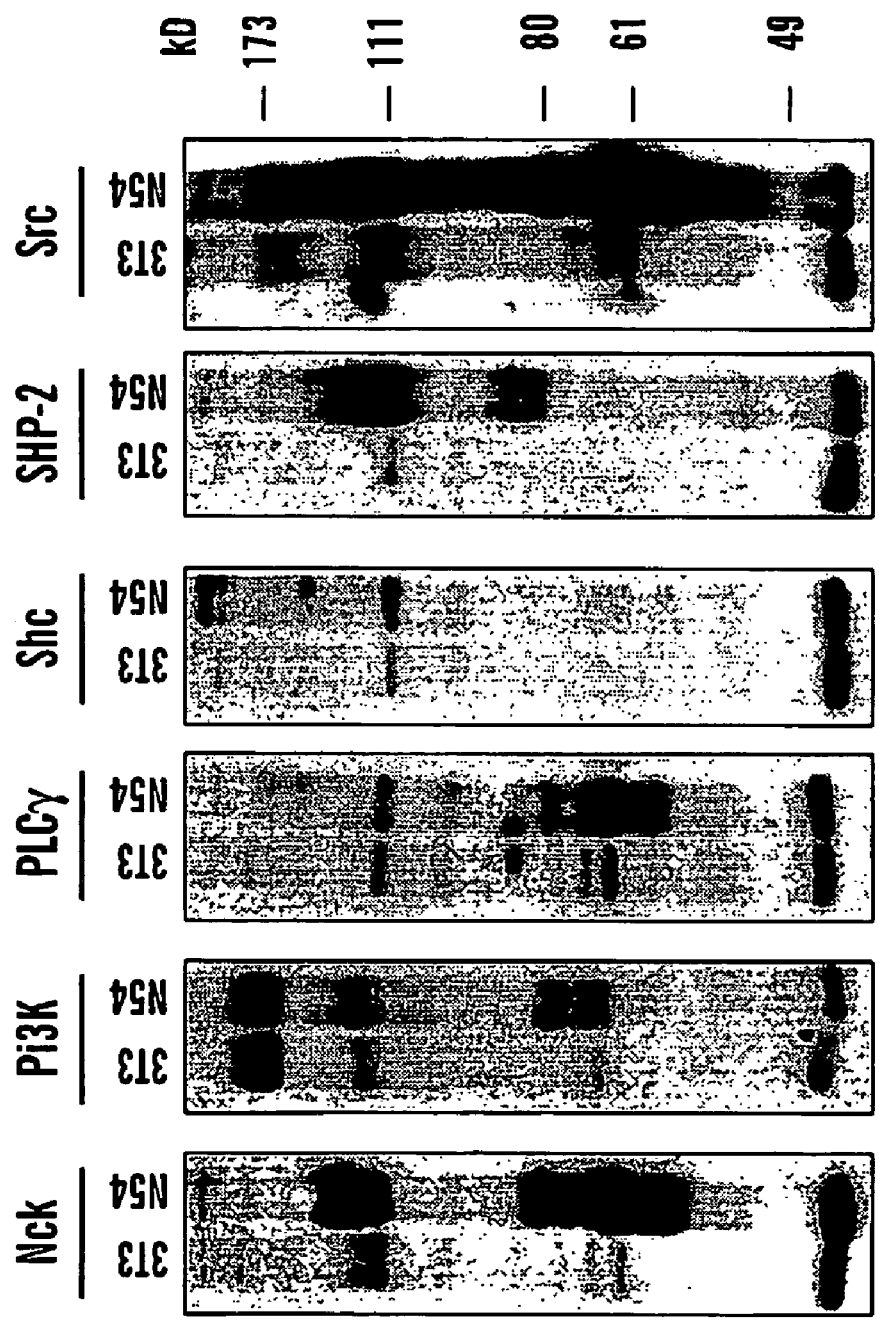
Figure 9:
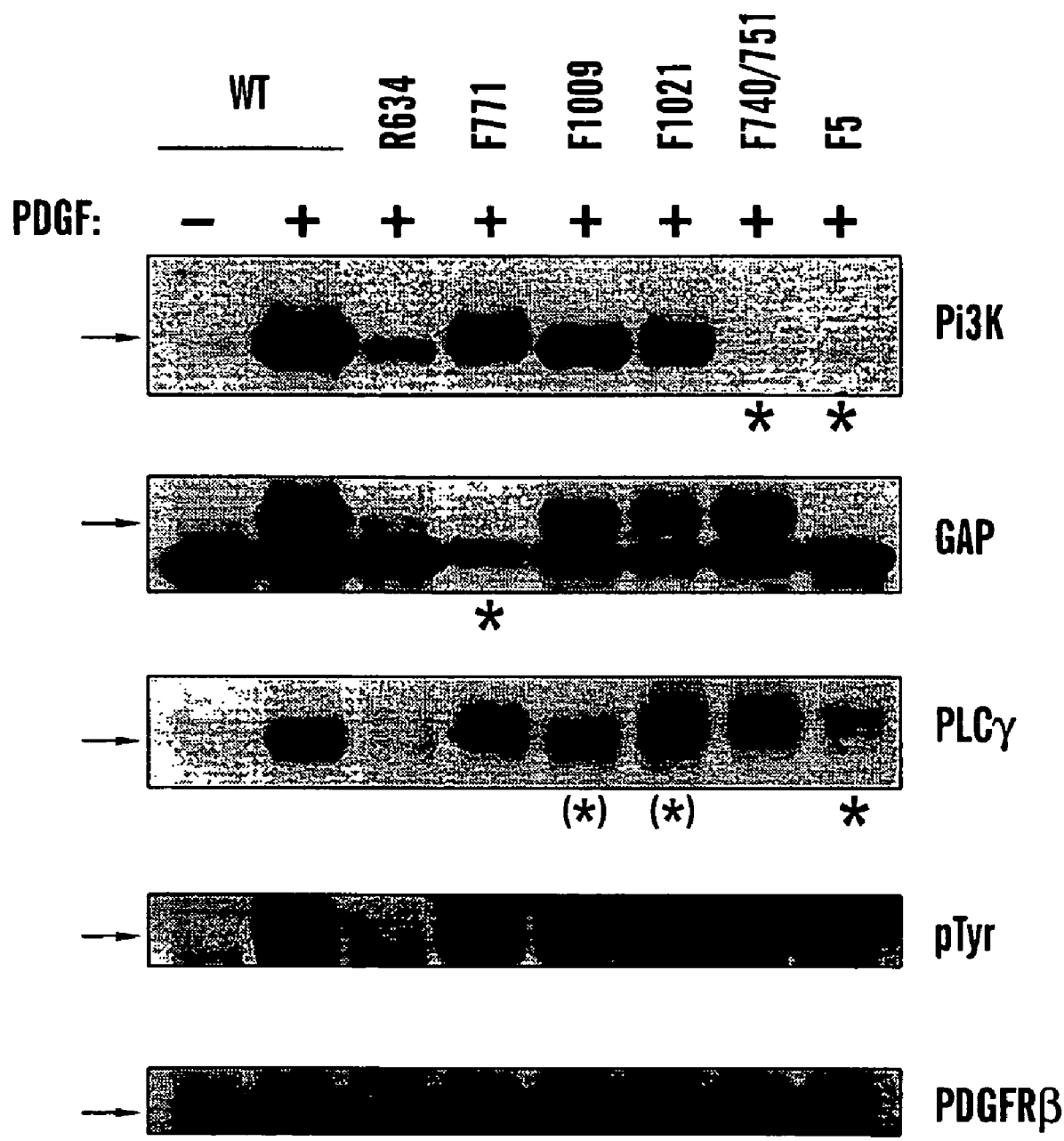
FIG. 9 shows binding studies of the SH2-domains of Pi3K, Gap and PLC-gamma to whole cellular proteins of HepG2 cells expressing wild type (wt) and different mutations of the PDGFbeta-receptor (R634=kinase dead, F=tyrosine to phenylalanine exchange at different positions of the cytoplasmatic domain of the PDGF-receptor, F5=all 5 sites (771, 1009, 1021, 740 and 751 are mutated)).
Figure 10A:
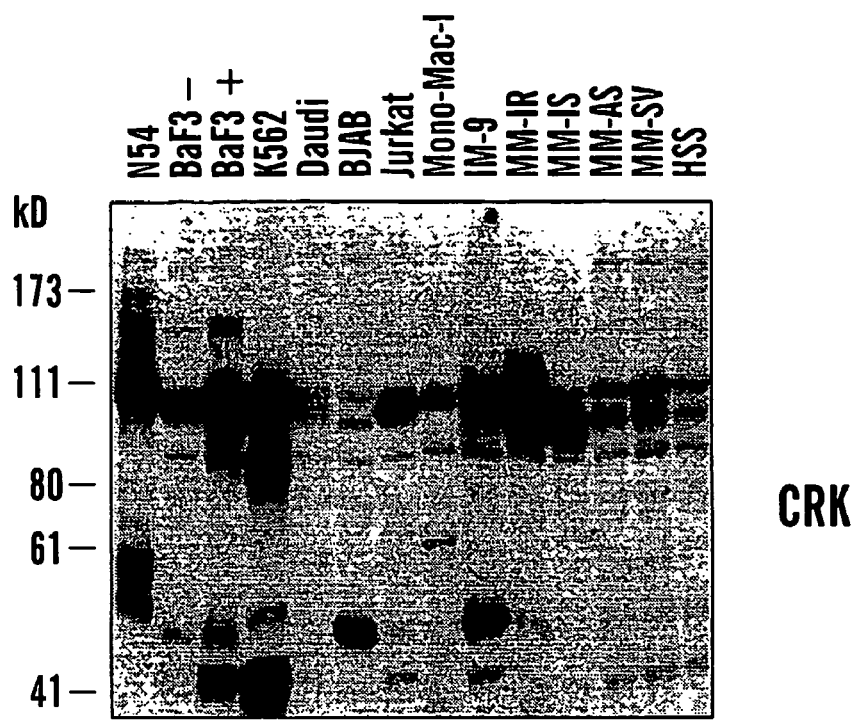
FIGS. 10A-D show SH2-domain binding patterns of Crk (FIG. 10A), Grb2 (FIG. 10B), Pi3-kinase (FIG. 10C), and pTyr (FIG. 10D) under competitive conditions in different malignant hematopoietic cell lines, v-abl transformed 3T3-cells (N54) and BCR-Abl inducible BaF3 cells. pTyr is an anti-phosphotyrosine blot. K562 cells are derived from chronic myeloid leukemia, Daudi and BJAB from Burkitt-Lymphoma, Jurkat from T-Cell-Lymphoma, Mono-MAC-1 from acute monocytic leukemia and IM-9, MM-IR, MM-IS, MM-AS, MM-SV as well as HSS represent different multiple myeloma cell lines.
Figure 10B:
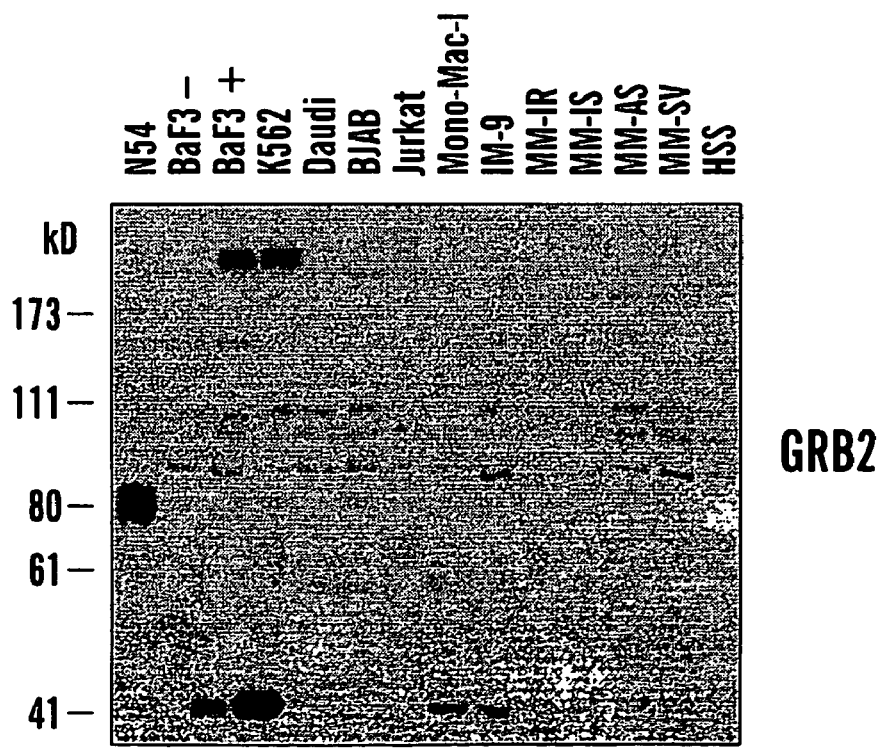
Figure 10C:
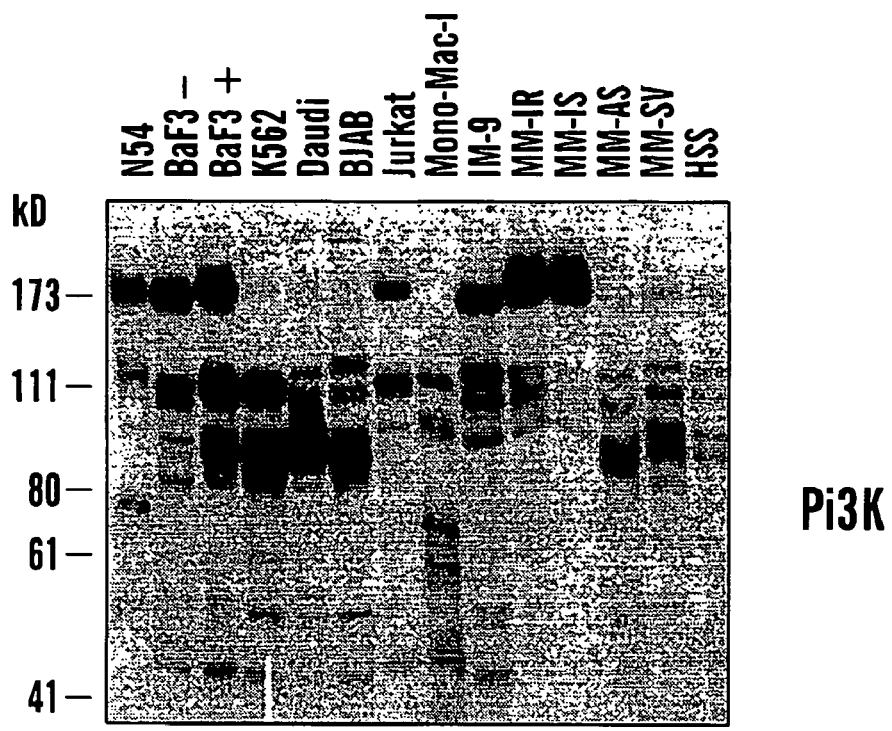
Figure 10D:
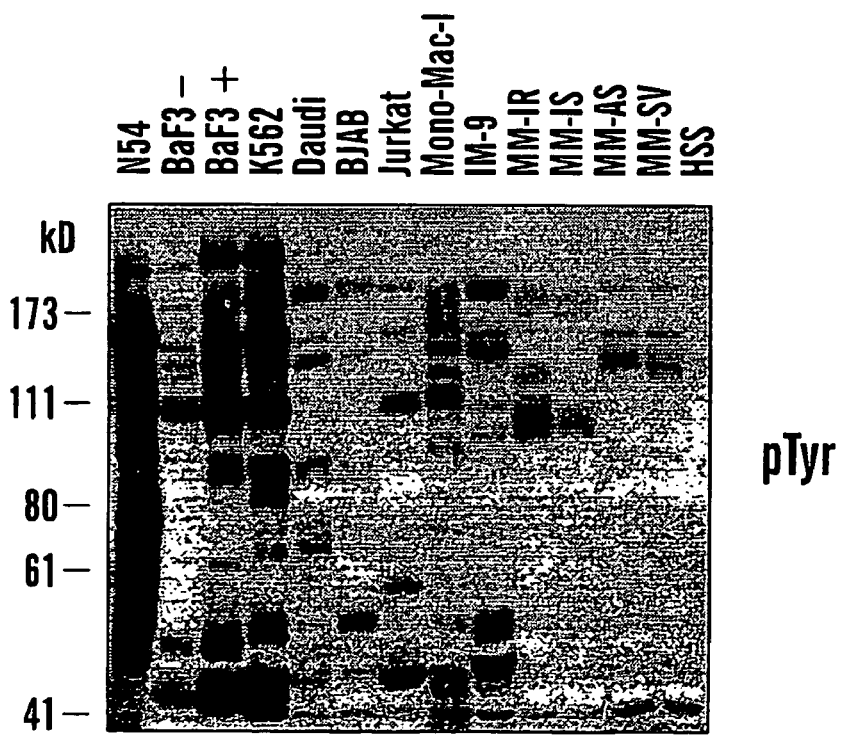
Figure 11A:
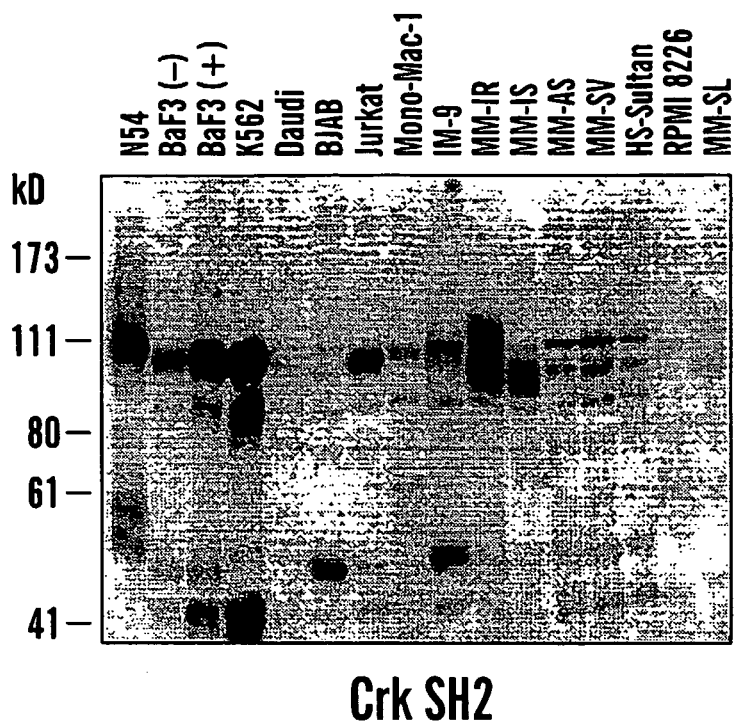
FIGS. 11A-F show whole cell lysates from human hematopoietic cell lines were separated by SDS-PAGE, transferred to membranes, probed with SH2 domains under competitive conditions or anti-phosphotyrosine antibody (anti-PTyr) as labeled, and bound probe detected by ECL. Migration of prestained molecular weight markers indicated on left. N54: v-Abl-transformed NIH-3T3 cell lysate (⅕ of the amount of protein compared to human cell line samples). BaF3(−) and BaF3(+): BaF3 cells expressing BCR-Abl under the control of an inducible promoter, without and with induction respectively. MM-IR and MM-IS are bone marrow-derived multiple myeloma lines that are resistant and sensitive to dexamethasone, respectively. MM-AS, MM-SV, and MM-SL are plasma cell leukemia lines.
Figure 11B:
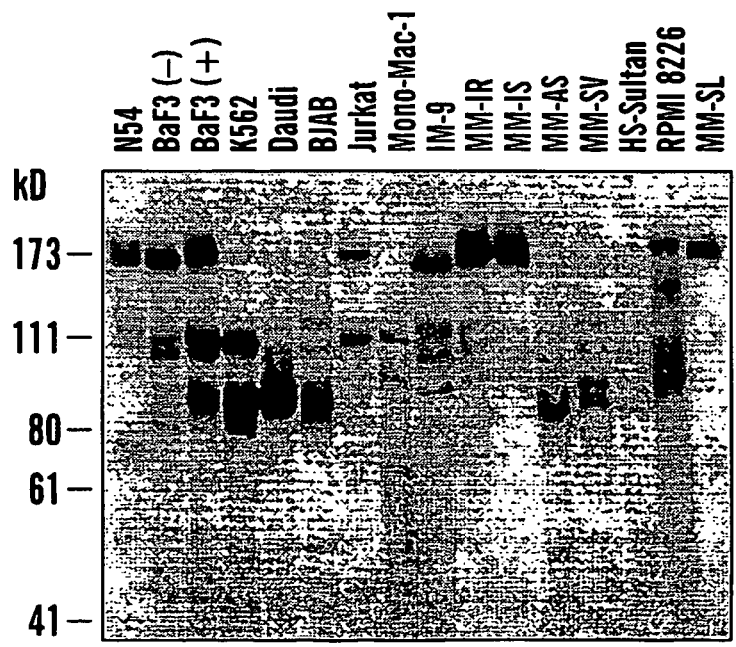
Figure 11C:
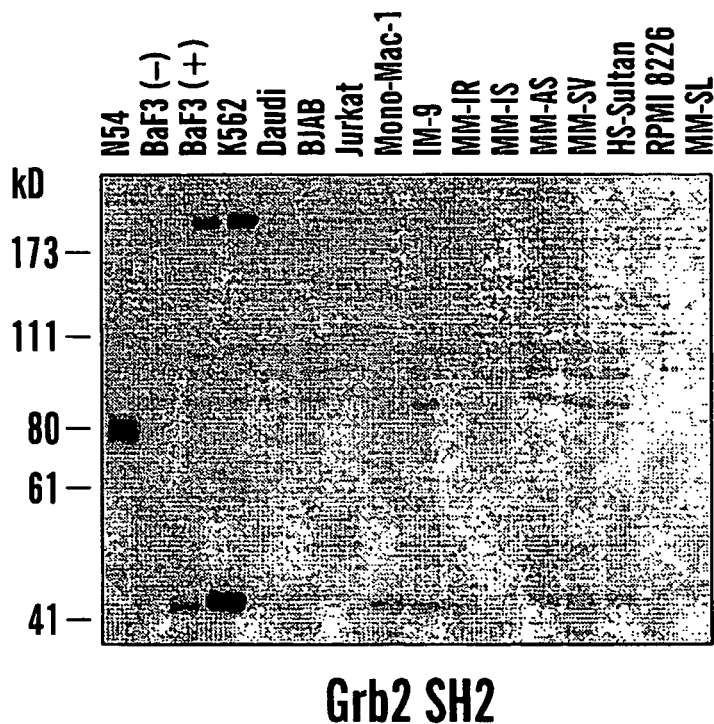
Figure 11D:
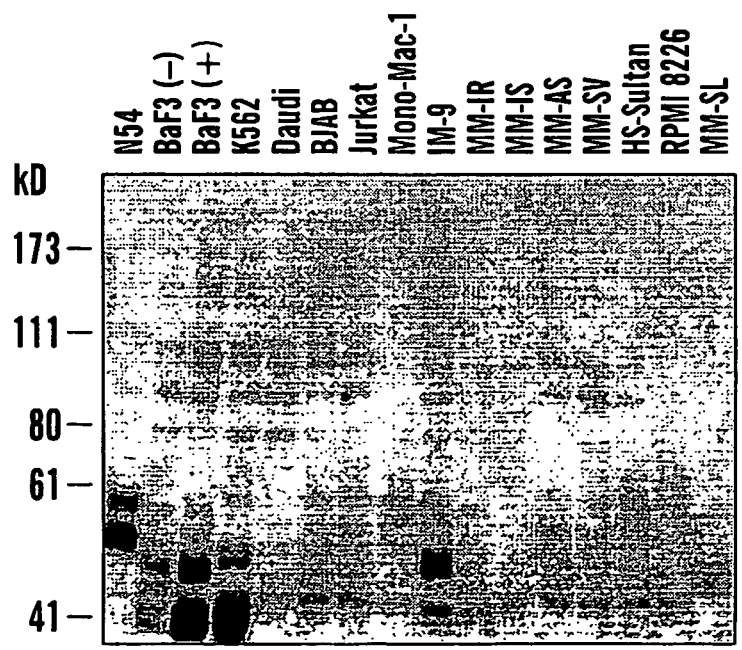
Figure 11E:
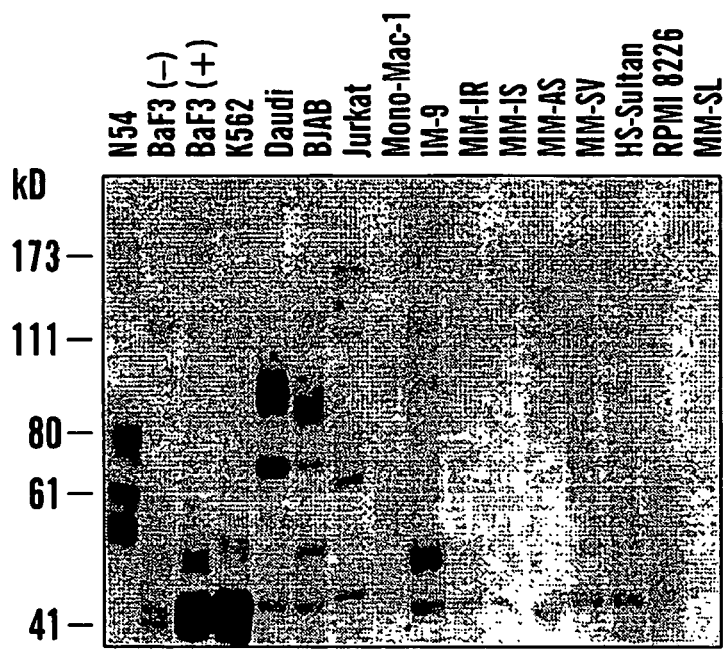
Figure 11F:
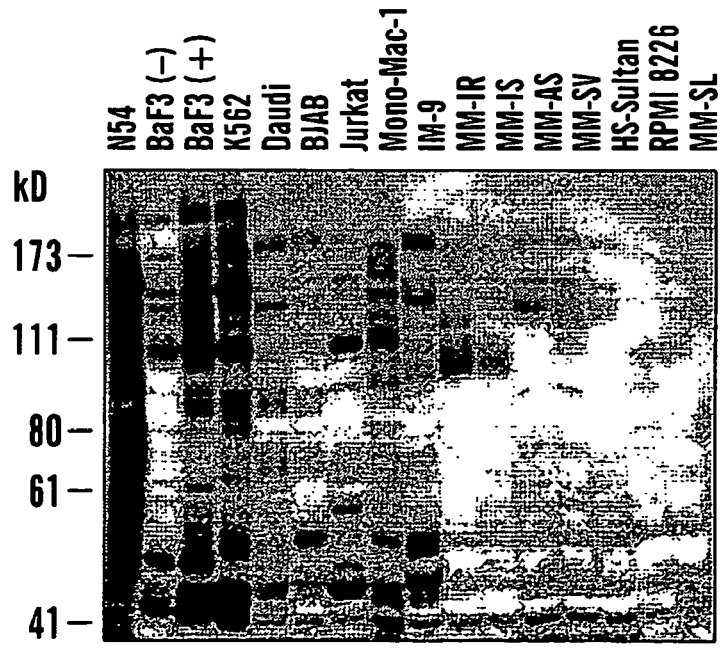

After establishing an appropriate method for the blocking of binding of GSH-HRP to competing binding domains, we were able to test the competitive binding assay of the present invention. Single GSH-HRP labeled SH2-domains were applied to a Far Western blot in the presence of three different unlabeled SH2-domains in which the GSH-binding site was previously blocked by the preincubation with GSH and ethacrynic acid. Whole cellular proteins of 3T3 and v-abl transformed 3T3 fibroblasts were used as a model system as described above. Patterns of tyrosine phosphorylation were different when the labeled Abl SH2 domain was incubated with the unlabeled domains of Crk, Gap and Grb2 compared to the patterns observed for the labeled SH2-domains of Crk or Gap co-incubated with the unlabeled SH2-domains of Abl, Crk, Gap and Grb2, respectively (FIG. 8). The data demonstrate that differential signaling profiles can be detected when different labeled and unlabeled protein-protein interactions domains are simultaneously applied in Far-Western blots, proving that the competitive assay of the present invention can be applied for the identification and quantification of cell-type specific protein-protein interaction profiles.

Moreover, the competitive assay of the present invention can be applied not only to protein-protein interaction domains, but to proteins and antibodies. It will be of great interest which differences in the signaling profile are detectable when this assay is applied, for example, for the analysis of clinical specimen like leukemia. Such profiles are useful for the molecular diagnosis of cell and tissue samples, for example in classifying histologically similar tumors.

Further Applications for the Novel Labeling Method

In principle, the method of the present invention to covalently attach GSH to GST fusion proteins using ethacrynic acid can be applied to any molecule that was previously conjugated with GSH. Conjugation of GSH to proteins is achieved by standard methods such as succinimide ester- or maleimide-mediated covalent attachment to the free sulfhydry of reduced GSH. This allows, for example, the covalent coupling of different protein-protein interaction domains to different fluorophores or other labels that have been previously conjugated with GSH. These probes can then be simultaneously applied in a single competitive binding reaction and the individual protein-protein interactions determined by, for example, fluorescence imaging utilizing the different excitation and emission spectra of the fluorophores for differential detection.

For "multiplexing," there should be a covalent or near-covalent attachment. For example, GSH and fluorophore both conjugated to a carrier protein, which is covalently linked to GST by chemical crosslinking; or GST fusion is biotinylated at unique site, and fluorophore coupled to streptavidin which binds very tightly to biotin; etc. The "multiplexing" approach is obviously not limited to the determination of signaling profiles of protein preparations immobilized on solid surfaces but can also be applied in a competitive fashion for the detection of protein-protein interactions in other settings, for example, individual cells. For this purpose, cells are either grown in tissue culture on appropriate surfaces or tissue sections are used, the cells are fixed, made permeable, and subsequently incubated with different labeled probes allowing the subcellular localization of specific binding partners to be determined by fluorescence microscopy.

Moreover, the labeling method of the present invention can be used for labeling of a large number of protein-protein interaction domains with different DNA-oligonucleotides as already described above. For example, biotinylated oligonucleotides that are unique in their internal base composition are bound to a solid support (e.g., streptavidin) to which GSH was previously attached. To ensure that only active and correctly folded proteins are labeled, covalently-linked probes are, preferably, further purified by a round of binding to GSH agarose, and then only that fraction that can bind is eluted. Each DNA-GSH-streptavidin complex is then coupled to individual biotinylated protein-protein interaction domains by incubation with ethacrynic acid. The extremely high affinity of the streptavidin-biotin interaction ($k_d$ approx. $10^{-14}$ M) makes this coupling essentially irreversible. The different labeled domains are purified and applied in a single binding reaction to immobilized proteins allowing the identification of protein-protein interactions by, for example, reverse dot blot or on DNA chips as described above.

The novel approach of the present invention for the analysis of binding interaction profiles is based on the binding of a large number of different protein-protein interaction domains to their corresponding binding partners in a competitive fashion allowing the identification of high affinity interactions. Analysis of complex protein-protein interactions can be realized when labeling and detection is performed with the newly established labeling techniques described herein. The assay can be widely used for the characterization and quantification of protein-protein interactions in various systems and can be applied to the detection of disease-related differences in cellular signaling pathways with the potential for the discovery and development of new prognostic markers or therapeutic strategies for the treatment of diseases.

All publications, patent applications, patents and other references mentioned herein are incorporated by reference in their entirety. In addition, the materials, methods and examples are illustrative only and not intended to be limiting. In case of conflict, the present specification, including definitions, controls.

REFERENCES

1. Sudol, M. From Src Homology domains to other signaling modules: proposal of the protein recognition code. Oncogene. 17: 1469-74, 1998.
2. Pawson, T. and Nash, P. Protein-protein interactions define specificity in signal transduction, Genes Dev. 14: 1027-47, 2000.
3. Mayer, B. J., Jackson, P. K., and Baltimore, D. The non-catalytic src homology region 2 segment of abl tyrosine kinase binds to tyrosine-phosphorylated cellular proteins with high affinity, Proc Natl Acad Sci USA. 88: 627-31, 1991.
4. Wood, E. R., McDonald, O. B., and Sahyoun, N. Quantitative analysis of SH2 domain binding. Evidence for specificity and competition, J Biol Chem. 267: 14138-44, 1992.
5. Luttrell, D. K., Lee, A., Lansing, T. J., Crosby, R. M., Jung, K. D., Willard, D., Luther, M., Rodriguez, M., Berman, J., and Gilmer, T. M. Involvement of pp60c-src with two major signaling pathways in human breast cancer, Proc Natl Acad Sci USA. 91: 83-7, 1994.
6. Kaelin, W. G., Jr., Pallas, D. C., DeCaprio, J. A., Kaye, F. J., and Livingston, D. M. Identification of cellular proteins that can interact specifically with the T/E1A-binding region of the retinoblastoma gene product, Cell 64: 521-32, 1991.
7. Zhao, Z., Manser, E., and Lim, L. Interaction between Pak and Nck: a template for Nck targets and role of Pak autophosphyorylation, Mol Cell Biol. 20: 3906-17, 2000.
8. Tanaka, S., Morishita, T., Hashimoto, Y., Hattori, S., Nakamura, S., Shibuya, M., Matuoka, K., Takenawa, T., Kurata, T., Nagashima, K., and Matsuda, M. C3G, a guanine nucleotide-releasing protein expressed ubiquitously, binds to the src homology 3 domains of CRK and GRB2/ASH protein, Proc Natl Acad Sci USA. 91: 3443-47, 1994.
9. Rabin, D. U., Palmer-Crocker, R., Mierz, D. V., Yeung, K. K. An ELISA sandwich capture assay for recombinant fusion proteins containing glutathione-S-transferase, J Immunol Methods. 156: 101-5, 1992.
10. Walker, J., Crowley, P., Moreman, A. D., and Barrett, J. Biochemical properties of cloned glutathione S-transferases from *Schistosoma mansoni* and *Schistosoma japonicum*, Mol Biochem Parasitol. 61: 255-64, 1993.
11. Ploemen, J. H., van Ommen, B., val Bladeren, P. J. Inhibition of rat and human glutathione S-transferase isoenzymes by ethacrynic acid and its glutathione conjugate, Biochem Pharmacol. 40: 1631-5, 1990.

What is claimed is:

1. A method for determining binding of a selected protein-protein interaction domain to a complementary binding partner of said selected protein-protein interaction domain present on a protein obtained from a biological specimen comprising:
   (a) obtaining a protein mixture from the biological specimen;
   (b) immobilizing the proteins of said protein mixture to a solid support;
   (c) contacting the immobilized proteins with a plurality of different unlabeled protein-protein interaction domains under appropriate binding conditions, wherein the different unlabeled protein-protein interaction domains are contacted with the immobilized proteins in the same binding reaction;

(d) simultaneously with or subsequent to step (c) contacting the immobilized proteins with at least one labeled selected protein-protein interaction domain, under appropriate binding conditions, wherein the label is selected from the group consisting of biotinylation sequences, antibody recognition sequences, glutathione-S-transferase tags, oligonucleotides, glutathione conjugates, fluorophores, and combinations thereof, the labeled protein-protein interaction domain being different from the unlabeled protein-protein interaction domains wherein the protein-protein interaction domains compete for binding to the immobilized proteins;

(e) washing away unbound labeled protein-protein interaction domain; and (f) detecting the binding of the labeled protein-protein interaction domain to a complementary binding partner of said selected protein-protein interaction domain wherein detection of said binding indicates the presence of a protein containing the complementary binding partner of said selected protein-protein interaction domain in said biological specimen.

2. The method of claim 1, wherein the solid support comprises a membrane, a plastic, or a bead.

3. The method of claim 1, wherein proteins in the protein mixture are denatured.

4. The method of claim 1, wherein proteins in the protein mixture are non-denatured.

5. The method of claim 1, wherein the labeled or unlabeled protein-protein interaction domains are selected from the group consisting of zinc finger, RING finger, WD40 repeat, armadillo repeat, ankyrin repeat, SH2-, SH3-, PTB-, PDZ-, WW-, EH-, LIM-, TPR-, SAM-, EVH1-.

6. The method of claim 1, wherein the labeled or unlabeled protein-protein interaction domains are SH2- or SH3-domains.

7. The method of claim 1, wherein a concentration of the labeled and unlabeled protein-protein interaction domains is greater than of the protein mixture.

8. The method of claim 1, wherein a single protein-protein interaction domain selected for binding is labeled, said label being selected from the group consisting of biotinylation sequences, antibody recognition sequences, glutathione-S-transferase tags, oligonucleotides, glutathione conjugates, and fluorophores.

9. The method of claim 1, wherein a plurality of different protein-protein-interaction domains selected for binding are differentially labeled.

10. The method of claim 1, wherein the label is glutathione-S-transferase (GST).

11. The method of claim 1, wherein the labeled or unlabeled protein-protein interaction domains are fusion proteins.

* * * * *